US005702468A

United States Patent [19]
Goldberg

[11] Patent Number: 5,702,468
[45] Date of Patent: Dec. 30, 1997

[54] CARPAL BONE BIAXIALLY RESTRAINED PROSTHESIS

[75] Inventor: Robert Goldberg, Campbell, Calif.

[73] Assignee: Uresil Corporation, Skokie, Ill.

[21] Appl. No.: 401,448

[22] Filed: Mar. 9, 1995

[51] Int. Cl.$^6$ .......................................... A61F 2/28
[52] U.S. Cl. .................................... 623/21; 623/16
[58] Field of Search ............................... 623/21, 16, 18

[56] References Cited

U.S. PATENT DOCUMENTS

| | | |
|---|---|---|
| 3,593,342 | 7/1971 | Niebauer . |
| 3,745,590 | 7/1973 | Stubstad . |
| 3,924,276 | 12/1975 | Eaton . |
| 3,973,277 | 8/1976 | Semple et al. . |
| 4,149,277 | 4/1979 | Bokros . |
| 4,164,793 | 8/1979 | Swanson . |
| 4,198,712 | 4/1980 | Swanson . |
| 4,450,591 | 5/1984 | Rappaport . |
| 4,936,854 | 6/1990 | Swanson . |
| 4,936,860 | 6/1990 | Swanson . |
| 4,955,915 | 9/1990 | Swanson . |
| 4,969,908 | 11/1990 | Swanson . |

*Primary Examiner*—Michael J. Milano
*Attorney, Agent, or Firm*—Laff, Whitesel, Conte & Saret, Ltd.

[57] ABSTRACT

A carpal bone prothesis comprising a body member made of a biocompatible, medically inert material which is designed to be restrained along at least two independent axes. In one important embodiment, the body member includes at least two independent channels and ingrowth receptive ligaments which extend through the channels and are attached to adjacent carpal bones along the first axis and to the dorsal and palmar capsules along the second axis.

67 Claims, 3 Drawing Sheets

CARPAL BONE BIAXIALLY RESTRAINED PROSTHESIS

FIELD OF THE INVENTION

This invention relates to carpal bone prostheses. More particularly, this invention relates to a prosthesis and a method for safely and effectively replacing the scaphoid or lunate bone in the wrist with a prosthesis tethered along multiple axes.

BACKGROUND OF THE INVENTION

Implants or prostheses are employed for restoring damaged carpal bones or joints in the wrists of human patients. These implants are especially useful in the repair of wrists which, for example, have been damaged by pathological conditions such as rheumatoid arthritis and aseptic necrosis, and for treating trauma which may have a debilitating effect on wrist bones.

Unfortunately, prior carpal implant designs have many drawbacks arising from their construction and from the fact that they act merely as spacers for replacing a damaged carpal bone. These prior designs fail primarily because they cannot reproduce the normal and vital ligamentous restraints of the carpal bones.

Wrist movement is apportioned between the radiocarpal and midcarpal joints in a very complex manner. Accordingly, it is essential that a carpal implant reproduce the natural synchronous motion between it and the adjacent carpal bones in order to preserve the shape of the implant and to prevent wear, fracture, dislocation and particulate synovitis.

The carpal implant most commonly available in the past has been made from silicone. Unfortunately, there are serious potential complications associated with the use of silicone in this and other medical applications. Indeed, since the scaphoid and lunate bones are the most stressed carpal bones, they are particularly susceptible to these complications, which affect the integrity of the surrounding carpal bone ligaments as well as joint motion. Thus, it is not surprising that many patients who have silicone carpal implants experience silicone-related complications such as foreign body giant cell synovitis, focal carpal bone destruction, fragmentation, fracture and subluxation.

Synovitis, mentioned above, is inflammation of the synovial membrane which lines and lubricates the wrist joint. It causes pain and inhibits wrist movement in bone joints. Violation of silicone implants with suturing techniques may contribute to fragmentation, debris and silicone-induced synovitis.

Focal carpal bone destruction is yet another complication which can arise at a later stage as a result of abnormal kinematics and synovitis over an extended period of time. Fragmentation and fracture of silicone implants and the resulting presence of silicone particulate debris results from implant stress related to implant translation subluxation or from implant fracture.

Finally, subluxation is a partial dislocation of the carpal bones. Subluxation and complete implant dislocation are complications which may result from the inherent lack of restraint of current carpal implants to their adjacent carpal bones. In the native carpus, restraint is by way of ligaments and capsule. Thickenings of the palmer and dorsal capsule have been anatomically designated as quasi-discrete ligaments called "extrinsic ligaments" (e.g., radio-scapho-capitate ligament). Whereas, those truly discrete interosseous ligaments which directly attach one carpal bone to another are called "intrinsic ligaments" (e.g. scapholunate ligaments). The intrinsic and extrinsic ligaments act dependently to synchronize the complex and balanced intercarpal kinematics. Currently available implants, including those made of titanium alloys, do not reproduce the restraining mechanisms of both the intrinsic and extrinsic ligaments, and therefore these prostheses are subject to subluxation and complete dislocation.

To date, a satisfactory technique for reconstruction of intercarpal ligaments and capsular restraints incorporating carpal replacements has not been achieved. While the present invention is uniquely designed to allow the surgeon to accurately and predictably reconstruct the necessary ligamentous restraints and thus prevent the above-mentioned causes of failure, the prior art fails to meet this need.

For example, in U.S. Pat. No. 3,745,590 an implant is disclosed which includes parallel ligamentous elements (defining a single plane) molded into the body of a prosthesis at approximately opposite ends of its top surface. The ligamentous elements are either sutured to adjacent collateral ligaments, tied to the nearest adjacent carpal bone, or tied to an incised ligament or tendon. These ligamentous elements attach the prosthesis along a single axis. This implant is not restrained in a second plane. This lack of restraint results in subluxation and increased shear.

The carpal metacarpal implant shown in the above-referenced '590 patent includes a stem portion that is integrally formed with the implant body and is adapted to fit into the medullary space in the metacarpal bone to be repaired. This implant includes at least one integral ligamentous element which can be tied or otherwise attached to an adjacent bone, ligament, or tendon. If the implant body includes more than one ligamentous element, the elements extend from a single opening along one edge of the implant body and are similarly tied to adjacent tissues, as described in relation to the first carpal implant above. This embodiment also only restrains the prosthesis along a single axis.

Yet another carpal implant is shown in U.S. Pat. No. 4,198,712. This implant includes a stabilizing stem that extends outwardly and generally perpendicularly to the surface of the implant. The stem is adapted to be inserted into an adjacent carpal bone for stabilizing the implant postoperatively. Wires or sutures may be used in conjunction with the stem for temporary fixation and enhanced stabilization of the implant during the early healing process. The wires or sutures are passed through the implant into adjacent carpal bones. The stem and the wires or sutures are intended to restrain the prosthesis along a single axis. Also, as noted earlier, suturing directly into silicone is disfavored as generally it is believed to avulse trailing silicone debris, potentially leading to silicone synovitis.

Accordingly, an object of the present invention is to provide a method and prosthesis for safely replacing a carpal bone in a human wrist.

It is another object of the present invention to provide a prosthesis for replacing a carpal bone which is suspended and tethered along multiple axes.

It is yet another object of the present invention to provide a prosthesis for replacing a carpal bone which despite the presence of effective restraint means encourages normal global carpal kinematics.

It is a further object of the present invention to provide a method and prosthesis for replacing a carpal bone which involves suturing the restraint means to both the palmar and dorsal capsules and to adjacent carpal bones by way of native intercarpal ligaments, or directly into bone by way of woven fabric, native capsule, bone-capsule-bone graft, or tendon.

These and other objects and advantages of the invention will appear hereinafter.

SUMMARY OF THE INVENTION

The present invention accomplishes the foregoing objects by providing a prosthesis comprising a generally spherical body member and ligamentous means.

The body member is made totally or partially from any appropriate biocompatible, medically inert material such as a ceramic, titanium, stainless steel alloys, or a non-ceramic substrate with a ceramic or other biocompatible, medically inert coating. It is contoured to resemble the shape of the carpal bone which it replaces, including the scaphoid bone or the lunate bone. In one preferred embodiment, the body member includes at least two independent channels which pass through the body member. The channels may intersect.

The ligamentous means may be attached within the body member channels by fibrous ingrowth into porous coating, by adhesive, or by other conventional means before the implant is placed in the wrist. However, in an alternative preferred embodiment, the ligamentous means are not secured within the channels. Rather, as discussed below, the body member is allowed minimal gliding motion on each ligamentous means while the combined effect of two or more ligamentous means produces a tethering suspension effect preventing significant translation of the body member.

In another alternative embodiment, the ligamentous means are first attached to each other near their midpoints, the channels in the body member intersect and the pre-attached ligamentous means are mounted in the intersecting channels. It is further preferred that the point of attachment of the ligamentous means be positioned at the point of intersection of the channels.

The ligamentous means may be native or artificial, and porous or non-porous. In one preferred embodiment, the ligamentous means comprise a porous woven fabric which is tissue ingrowth receptive for affixation to adjacent tissues by tissue ingrowth. Alternatively, native tissue such as capsular strips, bone-capsule-bone-graft, or palmaris longus tendon, for example, may be used as the ligamentous means. The ligamentous means preferably are sutured to the adjacent carpal bones by way of intercarpal ligament or by affixing the means into the cancellous bone itself.

The ligamentous means are positioned for tethering the prosthesis along at least two independent axes, thereby restraining translation while permitting limited necessary rotation of the body member. The first restraining axis is established when the prosthesis is attached to adjacent carpal bones. The second restraining axis is established when the prosthesis is attached to the dorsal and palmar capsules. This criss-cross tethering restraint mechanism prevents translation and destructive shear of the implant while permitting natural limited rotational motion in relation to adjacent carpal bones.

The above, as well as other objects and advantages of the invention, will become apparent from the following detailed description of the preferred embodiments as illustrated in the accompanying drawings.

DETAILED DESCRIPTION OF THE INVENTION

Figure 1:
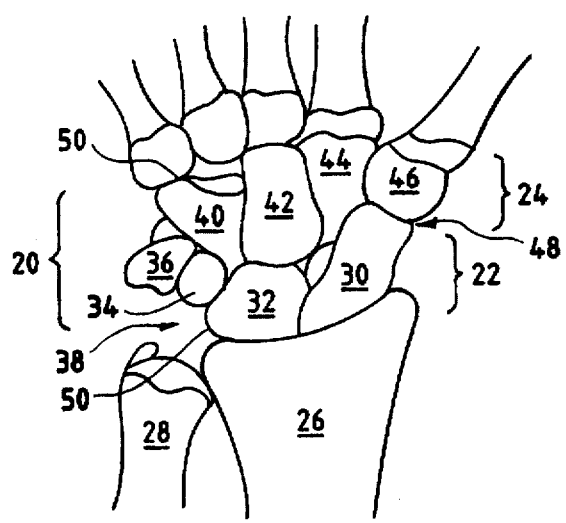
FIG. 1 is a plan view of the anterior or palmar side of the bones of the wrist joint of the right hand, shown palm up.

Generally referring to FIG. 1, an anterior or palmar view of the bones of the wrist carpus 20 of a right hand is shown, palm side up. The bones that form the carpus of the wrist 20 include a proximal carpal row 22 and a distal carpal row 24. Proximal carpal row 22 is adjacent the radius 26 and the ulna 28 of the wrist and includes a scaphoid bone 30, a lunate bone 32, a triquetrum bone 34, and a pisiform bone 36. The radial carpal joint 38 is that space between the proximal carpal row 22 and the articulating distal radius 26. The distal carpal row 24 includes a hamate bone 40, a capitate bone 42, a trapezoid bone 44, and a trapezium bone 46. The midcarpal joint 48 of the wrist extends between the distal and proximal carpal rows.

Figure 1A:
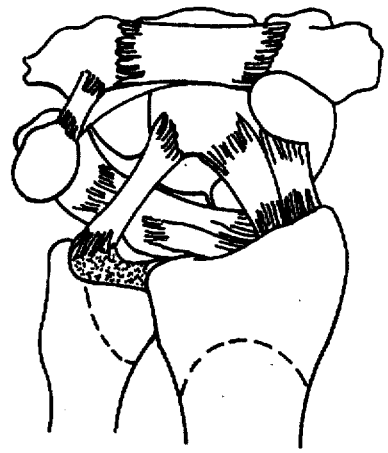
FIGS. 1A–1C are plan views respectively of the superficial palmar ligaments, the deep palmar ligaments and the dorsal ligaments.
Figure 1B:
Figure 1C:
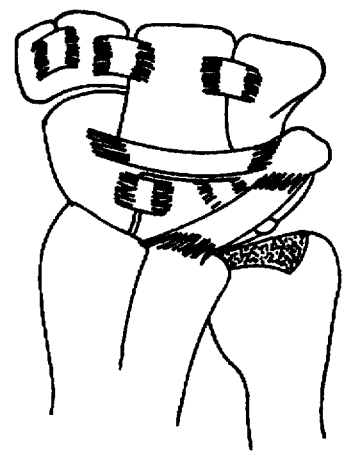

The extrinsic palmar carpal ligaments are shown in FIG. 1A, the intrinsic ligaments are shown in FIG. 1B and the dorsal extrinsic ligaments are shown in FIG. 1C.

Normal wrist movement is very complex and involves, in part, motion at the midcarpal joint and in part motion at the radiocarpal joint. Additionally, there is a predicable well orchestrated rotational motion specific and different for each carpal bone which is generated by the bone's shape and by its ligamentous and capsular attachments. For example, in radial deviation of the wrist the scaphoid distal pole rotates in a palmar direction, in a sense making "room" for the distal carpal row to pass over the proximal row. Likewise, in ulnar deviation the normal scaphoid rotates dorsally, away from the palm, tethered by its neighboring lunate and surrounding capsule, in a sense making "room" for the distal carpal row to pass more easily "under" the proximal row. In pathological conditions such as severe wrist sprains, the ligaments are disrupted and the synchronous carpal kinematics are impaired. This may lead to pain, arthritis and advanced collapse of the carpus, i.e., SLAC (Scapho-lunate advanced collapse) wrist. A similar fate of SLAC may occur secondarily to scaphoid fracture non-union or avascular necrosis. During the surgical replacement of a carpal bone (scaphoid or lunate) those ligaments which are not already disrupted must be cut. Unless those ligaments are reconstructed or substituted, the same fate may ensue: instability of the prosthesis, surrounding carpal arthritis and eventual carpal collapse. Too frequently this is the fate of current "unrestrained" carpal prostheses.

Figure 2A:
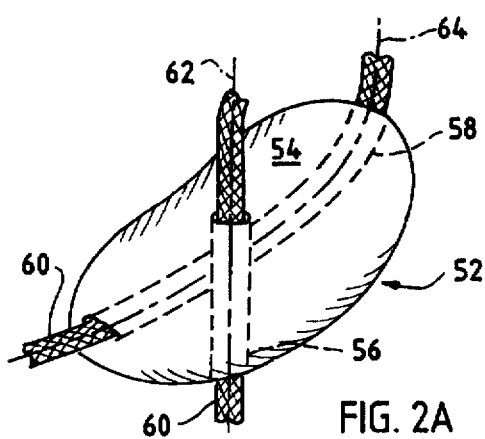
FIGS. 2A and 2B are perspective views of scaphoid and lunate carpal bone prostheses in accordance with the present invention.
Figure 2B:
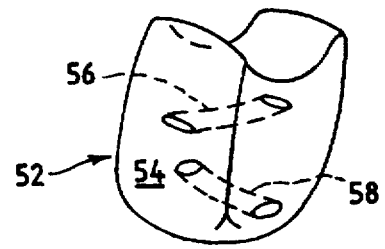

In accordance with the present invention, a "restrained" prosthesis, the complex carpal motion will be preserved and collapse with arthritis prevented. In FIGS. 2–6, the prosthesis is generally denoted by the numeral 52 and comprises a body member 54 contoured to resemble the shape of the carpal bone which it replaces. In FIGS. 2A and 2B, denoting respectively a scaphoid prosthesis and a lunate prosthesis, the body member includes first and second independent channels, 56 and 58, and ligamentous means 60 are positioned within the channels for tethering prosthesis 52 to adjacent tissues, including carpal bone as well as dorsal and palmar capsule.

Figure 3A:
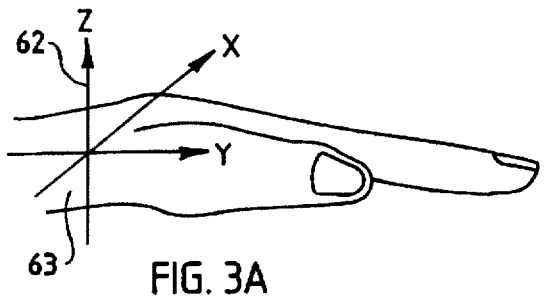
FIGS. 3A–3B are respectively side and top views of a human hand and wrist illustrating the positioning of the perpendicular x,y and z axes.
Figure 3B:
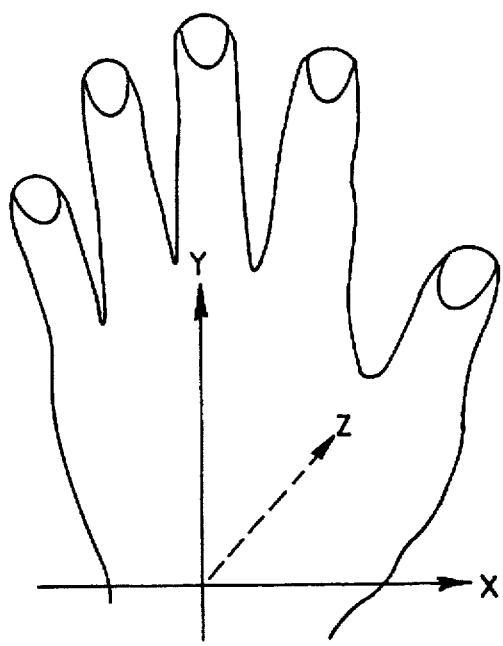

FIGS. 3A and 3B illustrate the three-dimensional structures of the carpus. The geometric axes of the hand, x, y and z axes are shown as 90° perpendicular planes of reference. To maintain reproducibility, for example on an x-ray, the following anatomic landmarks are chosen to create these axes: The x-axis represents a best fit line between the ulnar and radial styloids on a PA view. The y-axis is a best fit line through the length of the 3rd metacarpal shaft. The z-axis is simply a plane perpendicular to both the x and y axes. By creating these axes one has a mathematical tool and language to describe any coordinate or direction within the carpus. For example, each channel within a given carpal prosthesis has definable coordination on the x, y and z axes.

Returning now to FIG. 2A and continuing with the example of the scaphoid prosthesis, first channel 56 may be said in this embodiment to lie on an imaginary tether axis 62, essentially the z axis (dorsal to palmer) in FIGS. 3A and 3B. The second channel 58 (FIG. 2A) may be said in this embodiment to lie slightly obliquely to the x and y axes, articulating with the trapezium and lunate. In the preferred embodiment illustrated, channel 58 is curved to correspond generally to the curvature of the body member i.e., along its long axis, proximal pole to distal pole. Also, in the illustrated embodiment, channel 56 is substantially perpendicular to channel 58, and the two channels intersect at a single point within the body member. In alternative embodiments, the channels need not be intersecting, nor need they be completely perpendicular.

In FIG. 2A, each ligamentous means 60 extends through first and second channels 56 and 58, and emerges from the openings at each end of the channels. In the illustrated embodiments, the channels may be ovoid in cross-section in order to protect the body member against stress risers. The edge of each channel opening may be rounded to remove any sharp interface against the ligamentous means. Nevertheless, if desired, the channels may be circular or of any other cross-sectional shape which preserves the above desirable characteristics. Also, the channels may be used: 1) without a porous coating or other affixation means; 2) with a porous coating (70) to provide surface to facilitate tissue ingrowth between the ligamentous means and the prosthesis; or 3) with or without a porous coating, but with adhesive to anchor the ligamentous means.

Figure 4:
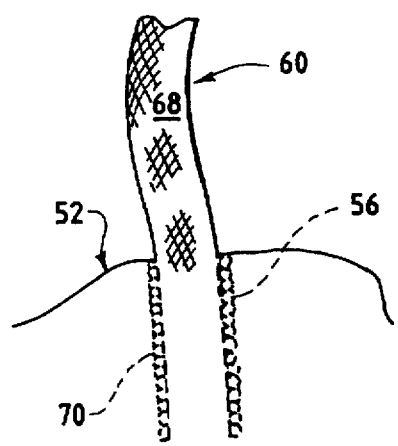
FIG. 4 is a partial cross-sectional view of the prosthesis of FIG. 2, illustrating the affixation of the ligamentous means within a channel by tissue ingrowth.

Ligamentous means 60 in FIG. 2A is placed through channels of the body member and is surgically attached to adjacent ligaments, capsule, or bone (see FIG. 4). Ligamentous means 60 may be made of Dacron or any other ingrowth receptive fabric (including Teflon), native tendon graft (e.g., palmerus longus), capsule, or bone-capsule-bone graft.

Figure 5:
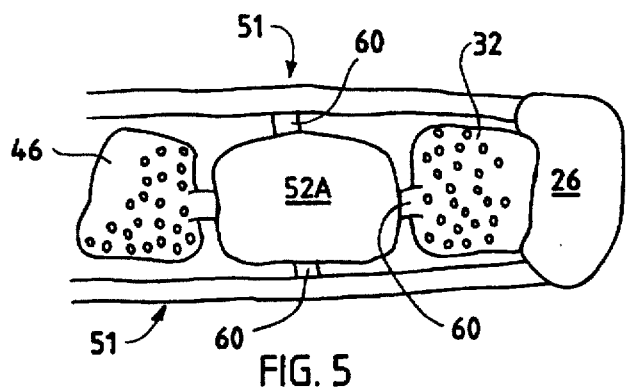
FIG. 5 is a partial side view of a scaphoid prosthesis, illustrating the affixation of the ligamentous means to adjacent carpal bones.
Figure 6:
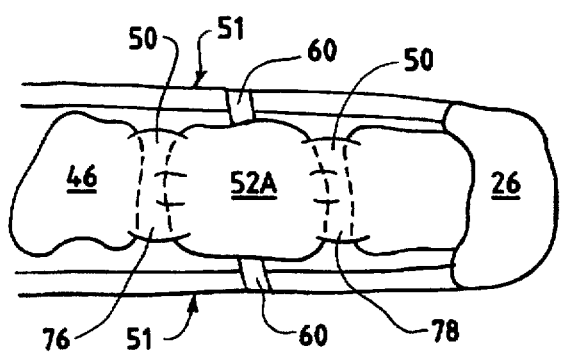
FIG. 6 is a partial side view of a scaphoid prosthesis, illustrating the affixation of the ligamentous means to adjacent carpal ligaments.

For example, when ligamentous means 60 are secured to an adjacent carpal bone (FIG. 5), various techniques may be used including suturing the ligamentous means directly to the adjacent intrinsic (interosseous) ligament. For example, ligamentous means 60 of a scaphoid prosthesis 52A could be sutured to the scaphotrapezial ligament 76 and the scapholunate ligament 78 which are located between trapezial bone 46 and scaphoid bone 30 (which has been replaced by prosthesis 52A) and scaphoid bone 30 (prosthesis 52A) and lunate bone 32, respectively, as shown in FIG. 6. An alternative technique would include removal of a very small area of cartilage and endosteum to expose raw cancellous bone. Drill holes would then be placed in the bone for passage of suture and a suture placed in the end of the ligamentous means. The suture would be passed through the drill holes pulling the ligamentous means firmly against, or through, the scarified bone and the sutures tied to each other in a horizontal mattress fashion. This technique of suturing is similar to that described by Julio Taleisnick, M.D. (*Journal of Hand Surgery*, 17A, March 1992, pages 354–359, "A Technique For Direct Repair of the Scapho-Lunate Interosseous Ligament"). An alternate technique to suture the ligamentous means to adjacent bone may include use of small bone anchors, e.g., Mitek® anchors which are available from Surgical Products, Inc. of Norwood, Mass., or to secure the ligamentous means by an interference screw. Similarly, the lunate prosthesis could be secured by ligamentous means in a similar fashion to its adjacent carpal bones, i.e., scaphoid (and/or scapholounate ligament) and the triquetrum (and/or lunotriquetral ligament).

Figure 7:
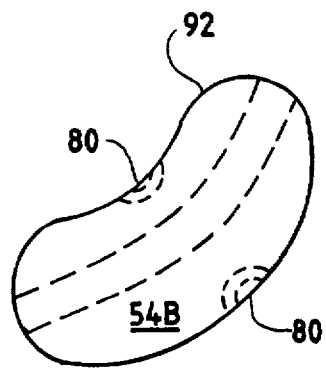
FIG. 7 is an alternate embodiment of the prosthesis of FIG. 2A in which ligamentous means are secured by means of eyelets.

In a less preferred alternate embodiment, body member 54B includes one or both of the ligamentous means secured to its outer periphery 92 by means of eyelets 80 (FIG. 7) movably restraining the prosthesis to adjacent tissues.

In use, prosthesis 52 is surgically implanted into a wrist for replacing a damaged carpal bone using standard surgical procedures. If the native intrinsic and extrinsic ligaments are intact, they are divided as the damaged carpal bone is removed, preserving neighboring ligament and capsular attachments. The properly sized prosthesis is then inserted into and properly positioned within the space created by the excised carpal bone such that one axis of the ligamentous means 60 is oriented towards the palmar or dorsal capsule 51 (FIGS. 4–6). The prosthesis is next oriented along the second axis by inserting it in normal articulating alignment with its neighboring carpal bones. Those articulating ends represent the exits for the second tethering channel through which the ligamentous means have been placed. Finally, the ligamentous means are fixed to adjacent capsule and intrinsic (interosseous) ligament or bone (see FIGS. 4–6).

The following is a description of the method by which the ligamentous means through channel 56 is fixed to the dorsal and palmar capsule.

In this method, referring again to FIG. 2A, the ligamentous means through channel 58 attaching to bone substitute for the "intrinsic ligaments" (i.e., short interosseous ligaments), and the ligamentous means through channel 56 substitute for the extrinsic ligaments (i.e., dorsal and palmar capsular attachments). In order to secure ligamentous means through channel 56 sutures attached to the ligamentous means at each end may be sewn directly to capsule and at either or both ends. Alternatively, the suture may be brought through capsule, then skin, and tied down in a standard fashion over a button. After many weeks of healing the pull-out suture and button would be removed leaving the secured ligamentous means in place.

Figure 8:
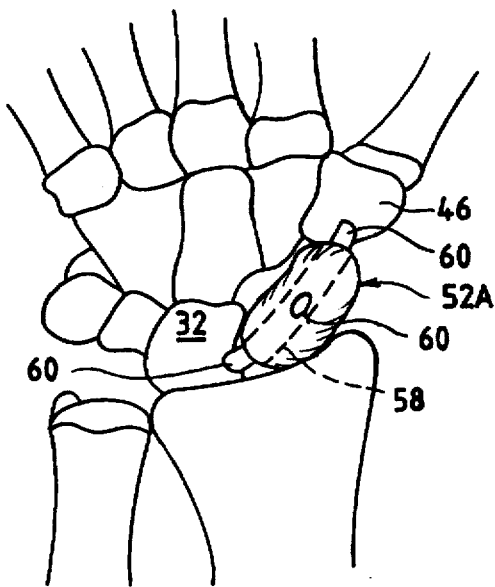
FIG. 8 is a plan view of a scaphoid prosthesis subsequent to its implantation in the wrist.
Figure 9:
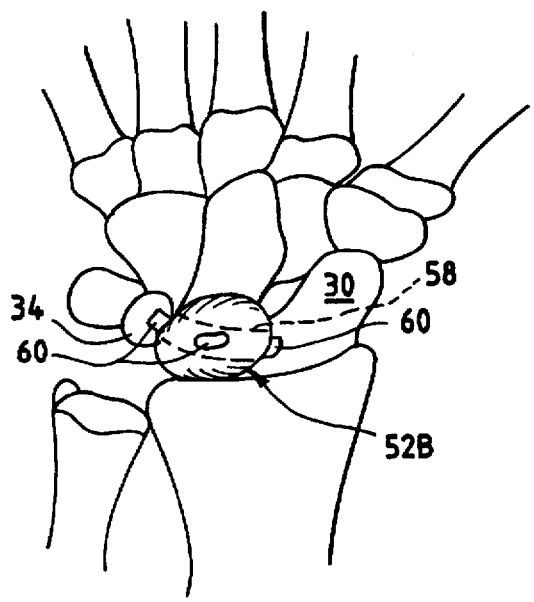
FIG. 9 is a plan view of a lunate prosthesis subsequent to its implantation in the wrist.

FIGS. 8 and 9 illustrate a scaphoid and lunate prosthesis, 52A and 52B, respectively, after to their implantation in a wrist. First referring to FIG. 8, scaphoid prosthesis 52A is tethered by ligamentous means 60 by way of channel 58, to trapezium bone 46 and lunate bone 32. Scaphoid prosthesis 52A is also tethered by a second ligamentous means 60 to the dorsal and palmar capsules by way of channel 56. This second ligamentous means would be perpendicular to the plane of the Figure (i.e., in and out of the plane of the paper). Referring to FIG. 9, lunate prosthesis 52B is shown tethered by way of its two channels by ligamentous means 60 to scaphoid bone 30 and triquetrum bone 34 and by the other ligamentous means to the dorsal and palmar capsules. Again, this second ligamentous means is illustrated perpendicular to the Figure.

Therefore, it should be recognized that, while the invention has been described in relation to a preferred embodiment thereof, those skilled in the art may develop a wide variety of structural details without departing from the principles of the invention. Accordingly, the appended claims are to be construed to cover all equivalents falling within the scope and spirit of the invention.

The invention claimed is:

1. A surgically implantable carpal bone prosthesis comprising:
    a biocompatible, medically inert body member contoured to resemble the shape of the carpal bone which it is to replace; and
    means for restraining said body member along crisscrossing axes which pass through the body member, the body member including at least two independent channels passing therethrough along the independent axes and the restraining means comprising ligamentous means passing through the channels.

2. The carpal bone prosthesis of claim 1 in which the body member is made from a material chosen from the group consisting of ceramic, titanium, or stainless steel alloys.

3. The carpal bone prosthesis of claim 1 in which the body member comprises a non-ceramic substrate with a ceramic or other biocompatible, medically inert coating.

4. The carpal bone prosthesis of claim 1 in which the body member is contoured to resemble the shape of a scaphoid bone.

5. The carpal bone prosthesis of claim 1 in which the body member is contoured to resemble the shape of a lunate bone.

6. The carpal bone prosthesis of claim 1 in which the crisscrossing axes do not intersect.

7. The carpal bone prosthesis of claim 1 including adjacent carpal bones and capsule in which the restraining means comprise ligamentous means attached to adjacent carpal bones and to capsule which pass through the body member within the two channels.

8. The carpal bone prosthesis of claim 1 in which the ligamentous means have an open pore surface which is tissue ingrowth receptive for anchoring the ligamentous means within the channels.

9. The carpal bone prosthesis of claim 1 in which the ligamentous means comprise native tissue.

10. The carpal bone prosthesis of claim 1 in which ligamentous means through the first channel are attached to adjacent carpal bones and ligamentous means through the second channel are attached to the dorsal and palmar capsules.

11. The carpal bone prosthesis of claim 1 in which the ligamentous means are anchored within the channels with adhesive.

12. The carpal bone prosthesis of claim 1 in which the restraining means comprise ligamentous means secured to the periphery of the body member along the two independent axes.

13. The carpal bone prosthesis of claim 1 in which at least two of the channels intersect within the body member.

14. The carpal bone prosthesis of claim 12 in which the ligamentous means are secured to the outer periphery of the body member by eyelets.

15. The carpal bone prosthesis of claim 1 in which the edges of the channel openings are rounded.

16. The carpal bone prosthesis of claim 1 in which the channels have a porous coating.

17. The carpal bone prosthesis of claim 1 in which the ligamentous means are in the form of a rounded cord.

18. The carpal bone prosthesis of claim 1 in which the channels are ovoid in cross-section.

19. A method for replacing a damaged carpal bone in a human wrist with a carpal bone prosthesis comprising:
    removing the damaged carpal bone;
    positioning a biocompatible, medically inert body member contoured to resemble the shape of the carpal bone which it is to replace at the site formerly occupied by the damaged carpal bone, said body member having at least two criss-crossing channels; and
    permanently restraining the body member along at least two independent axes passing through the criss-crossing channels using ligamentous means anchored within the channels by adhesive, by porous coating ingrowth, or by both adhesive and porous coating ingrowth.

20. The method of claim 19 in which the body member channels do not intersect.

21. The method of claim 19 in which the ligamentous means have an open pore surface which is tissue in-growth receptive.

22. The method of claim 19 in which the ligamentous means are anchored within the channels by means of adhesive.

23. The method of claim 19 in which the channels are ovoid in cross-section.

24. The method of claim 19 in which the edges of the channel openings are rounded.

25. The method of claim 19 in which the channels have a porous coating.

26. The method of claim 19 in which the ligamentous means are flat.

27. The method of claim 19 in which the ligamentous means are in the form of a rounded cord.

28. A method for replacing a damaged carpal bone in a human wrist with a carpal bone prosthesis comprising:
    removing the damaged carpal bone;
    positioning a biocompatible, medically inert body member contoured to resemble the shape of the carpal bone which it is to replace at the site formerly occupied by the damaged carpal bone, said body member having at least two criss-crossing channels; and
    permanently restraining the body member along at least two independent axes passing through the criss-crossing channels having a porous coating.

29. A surgically implantable carpal bone prosthesis comprising:
    a biocompatible, medically inert body member contoured to resemble the shape of the carpal bone which it is to replace; and
    means for restraining said body member along two intersecting axes which pass through the body member and channels passing therethrough along the intersecting axes, said restraining means comprising ligamentous means passing through the channels.

30. The carpal bone prosthesis of claim 29 in which the body member is made from a material chosen from the group consisting of ceramic, titanium, or stainless steel alloys.

31. The carpal bone prosthesis of claim 29 in which the body member comprises a non-ceramic substrate with a ceramic or other biocompatible, medically inert coating.

32. The carpal bone prosthesis of claim 29 in which the body member is contoured to resemble the shape of a scaphoid bone.

33. The carpal bone prosthesis of claim 29 in which the body member is contoured to resemble the shape of a lunate bone.

34. The carpal bone prosthesis of claim 29 in which the ligamentous means are attached to adjacent carpal bones and to capsule.

35. The carpal bone prosthesis of claim 29 in which the ligamentous means have an open pore surface which is tissue ingrowth receptive for anchoring the ligamentous means within the channels.

36. The carpal bone prosthesis of claim 29 in which the ligamentous means comprise native tissue.

37. The carpal bone prosthesis of claim 29 in which ligamentous means through the first channel are attached to adjacent carpal bones and ligamentous means through the second channel are attached to the dorsal and palmar capsules.

38. The carpal bone prosthesis of claim 29 in which the ligamentous means are anchored within the channels with adhesive.

39. The carpal bone prosthesis of claim 29 in which the ligamentous means are secured to the periphery of the body member along the two independent axes.

40. The carpal bone prosthesis of claim 36 in which the ligamentous means are secured to the outer periphery of the body member by eyelets.

41. The carpal bone prosthesis of claim 29 in which the edges of the channel openings are rounded.

42. The carpal bone prosthesis of claim 29 in which the channels have a porous coating.

43. The carpal bone prosthesis of claim 29 in which the ligamentous means are in the form of a rounded cord.

44. The carpal bone prosthesis of claim 29 in which the channels are ovoid in cross-section.

45. A surgically implantable carpal bone prosthesis comprising:

a biocompatible, medically inert body member contoured to resemble the shape of the carpal bone which it is to replace; and means for restraining said body member along at least two independent channels having a porous coating which pass through the body member, said restraining means comprising ligamentous means passing through the channels.

46. The carpal bone prosthesis of claim 45 in which the body member is made from a material chosen from the group consisting of ceramic, titanium, or stainless steel alloys.

47. The carpal bone prosthesis of claim 45 in which the body member comprises a non-ceramic substrate with a ceramic or other biocompatible, medically inert coating.

48. The carpal bone prosthesis of claim 45 in which the body member is contoured to resemble the shape of a scaphoid bone.

49. The carpal bone prosthesis of claim 45 in which the body member is contoured to resemble the shape of a lunate bone.

50. The carpal bone prosthesis of claim 45 in which the ligamentous means are attached to adjacent carpal bones.

51. The carpal bone prosthesis of claim 46 in which the ligamentous means have an open pore surface which is tissue ingrowth receptive for anchoring the ligamentous means within the channels.

52. The carpal bone prosthesis of claim 46 in which the ligamentous means comprise native tissue.

53. The carpal bone prosthesis of claim 46 in which ligamentous means through the first channel are attached to adjacent carpal bones and ligamentous means through the second channel are attached to the dorsal and palmar capsules.

54. The carpal bone prosthesis of claim 46 in which the ligamentous means are anchored within the channels with adhesive.

55. The carpal bone prosthesis of claim 46 in which at least two of the channels intersect within the body member.

56. The carpal bone prosthesis of claim 46 in which the edges of the channel openings are rounded.

57. The carpal bone prosthesis of claim 46 in which the ligamentous means are in the form of a rounded cord.

58. The carpal bone prosthesis of claim 46 in which the channels are ovoid in cross-section.

59. A method for replacing a damaged carpal bone in a human wrist with a carpal bone prosthesis comprising:

removing the damaged carpal bone;

positioning a biocompatible, medically inert body member contoured to resemble the shape of the carpal bone which it is to replace at the site formerly occupied by the damaged carpal bone, said body member having at least two independent channels with a porous coating; and restraining the body member along at least two independent axes passing through the independent channels.

60. The method of claim 59 in which ligamentous means are used to restrain the body member.

61. The method of claim 60 in which the ligamentous means have an open pore surface which is tissue ingrowth receptive.

62. The method of claim 60 in which the ligamentous means are anchored within the channels by adhesive, by porous coating ingrowth, or by both adhesive and porous coating ingrowth.

63. The method of claim 60 in which the ligamentous means are anchored within the channels by means of adhesive.

64. The method of claim 59 in which the channels are ovoid in cross-section.

65. The method of claim 59 in which the edges of the channel openings are rounded.

66. The method of claim 59 in which the ligamentous means are flat.

67. The method of claim 59 in which the ligamentous means are in the form of a rounded cord.

* * * * *